United States Patent
Gibbs (10) Patent No.: US 12,350,256 B2
(45) Date of Patent: Jul. 8, 2025

(54) HISTIDINE AND/OR HISTIDINE DERIVATIVE FOR THE TREATMENT OF INFLAMMATORY SKIN DISEASES

(71) Applicant: Curapel (Scotland) Limited, Glasgow (GB)

(72) Inventor: Neil Kerslake Gibbs, Cheshire (GB)

(73) Assignee: CURAPEL (SCOTLAND) LIMITED, Glasgow (GB)

(*) Notice: Subject to any disclaimer, the term of this patent is extended or adjusted under 35 U.S.C. 154(b) by 46 days.

(21) Appl. No.: 17/545,331

(22) Filed: Dec. 8, 2021

(65) Prior Publication Data

US 2022/0096439 A1   Mar. 31, 2022

Related U.S. Application Data

(60) Continuation of application No. 14/950,559, filed on Nov. 24, 2015, now abandoned, which is a division of application No. 12/918,701, filed as application No. PCT/GB2009/000430 on Feb. 18, 2009, now abandoned.

(30) Foreign Application Priority Data

Feb. 20, 2008 (GB) ..................... 0803054

(51) Int. Cl.
- *A61K 31/4172* (2006.01)
- *A61P 17/00* (2006.01)
- *A61P 17/04* (2006.01)
- *A61P 17/06* (2006.01)

(52) U.S. Cl.
CPC .......... *A61K 31/4172* (2013.01); *A61P 17/00* (2018.01); *A61P 17/04* (2018.01); *A61P 17/06* (2018.01)

(58) Field of Classification Search
None
See application file for complete search history.

(56) References Cited

U.S. PATENT DOCUMENTS

| | | | |
|---|---|---|---|
| 3,472,931 A | 10/1969 | Stoughton | |
| 3,891,757 A | 6/1975 | Higuchi | |
| 3,970,750 A * | 7/1976 | Brockemeyer | A61K 9/0007 424/679 |
| 4,686,107 A | 8/1987 | Zimmerman et al. | |
| 5,614,202 A | 3/1997 | DeFina | |
| 5,723,482 A | 3/1998 | Degwert et al. | |
| 6,211,221 B1 | 4/2001 | Peterson et al. | |
| 6,329,414 B1 | 12/2001 | Thomas et al. | |
| 2002/0004072 A1 | 1/2002 | Thomas | |
| 2003/0191192 A1 | 10/2003 | Venus et al. | |
| 2004/0052826 A1 | 3/2004 | Fernandez-Kleinlein et al. | |
| 2005/0015124 A1 * | 1/2005 | Irwin | A61N 5/0616 607/94 |
| 2005/0143793 A1 | 6/2005 | Korman et al. | |
| 2006/0204552 A1 * | 9/2006 | Fray | A23K 20/163 514/423 |
| 2006/0251703 A1 | 11/2006 | Shiao | |
| 2010/0331235 A1 | 12/2010 | Gibbs | |
| 2016/0074365 A1 | 3/2016 | Gibbs | |

FOREIGN PATENT DOCUMENTS

| | | | |
|---|---|---|---|
| DE | 4307983 A1 | 9/1994 | |
| DE | 4328871 A1 | 3/1995 | |
| DE | 10141780 A1 | 3/2003 | |
| GB | 1001949 | 8/1965 | |
| GB | 1464975 | 2/1977 | |
| JP | 58164516 A | 9/1983 | |
| JP | 2005120007 A | 5/2005 | |
| JP | 2008031066 A | 2/2008 | |
| WO | 9505852 A1 | 3/1995 | |
| WO | 2004071208 A1 | 8/2004 | |
| WO | WO-2007052289 A2 * | 5/2007 | A61K 31/495 |
| WO | 2009103959 A2 | 8/2009 | |
| WO | 2009103959 A3 | 8/2009 | |

OTHER PUBLICATIONS

Catalog listing for "L-Histidine monohydrochloride monohydrate," http://www.sigmaaldrich.com/catalog/product/fluka/53370?lang=en&region=US, Mar. 31, 2002, 1 page, Sigma-Aldrich.
Certified United Kingdom priority application entitled "Medicament," filed Feb. 20, 2008 as United Kingdom Application No. 0803054.6.
Charman, Carolyn R., et al, "The Patient-Oriented Eczema Measure Development and Initial Validation of a New Tool for Measuring Atopic Eczema Severity from the Patients' Perspective," Arch. Dermatol., Dec. 2004, pp. 1513-1519, plus 1 correction pages, vol. 140, American Medical Association.
Claxton, A. J., et al., "A Systematic Review of the Associations Between Doe Regimens and Medication Compliance," Clinical Therapeutics, 2001, pp. 1296-1310, vol. 23, No. 8.

(Continued)

*Primary Examiner* — Bethany P Barham
*Assistant Examiner* — Peter Anthopolos
(74) *Attorney, Agent, or Firm* — Conley Rose, P.C.; Rodney B. Carroll (57) ABSTRACT

A method of maintaining and/or improving barrier function of the skin of a human subject is disclosed herein. An embodiment of the instant method includes orally administering to a subject in need of maintenance and/or improvement of skin barrier function an effective amount of histidine and/or a derivative thereof. In some embodiments, the method may be used on a subject requiring the treatment and/or prevention of a skin disorder or condition. The barrier skin function may be assessed by measuring transepidermal water loss and administering the histidine and/or the derivative thereof in a composition comprising from about 0.5 g to about 7 g total amount of the histidine and/or derivative thereof per single dose.

20 Claims, 2 Drawing Sheets

(56) References Cited

OTHER PUBLICATIONS

Dave, Vinay K., et al., "Reduced Skin Histidine Levels and Its Topical Use in Psoriasis," Letters to the Editor, Acta. Derm. Venereol (Stockh) 1987, pp. 274, 67.
De Fabo, Edward C., et al., "Mechanism of Immune Suppression by Ultraviolet Irradiation In Vivo, Evidence for the Existence of a Unique Photoreceptor in Skin and its Role in Photoimmunology," J. Exp. Med., Jul. 1983, pp. 84-98, vol. 157, The Rockefeller University Press.
Ehlers, C., et al., "Comparison of two pH meters used for skin surface pH measurement: the pH meter 'pH900' from Courage & Khazaka versus the pH meter '1140' from Mettler Toledo," Skin Research and Technology, 2001, pp. 84-89, 7, Munksgaard.
Filing receipt and specification for patent application entitled "Histidine and/or Histidine Derivative for the Treatement of Inflammatory Skin Diseases," by Neil Kerslake Gibbs., filed Nov. 24, 2015 as U.S. Appl. No. 14/950,559.
Fluhr, Joachim W., "Transepidermal water loss reflects permeability barrier status: validation in human and rodent in vivo and ex vivo models," Experimental Dermatology, 2006, pp. 483-492, 15, The Authors Journal Compilation, Blackwell Munksgaard.
Foreign communication from the priority application - International Search Report and Written Opinion, PCT/GB2009/000430, Aug. 27, 2009, 19 pages.
Foreign communication from the priority application—International Preliminary Report on Patentability, PCT/GB2009/000430, Aug. 24, 2010, 13 pages.
Fukuyama, Kimie et al., "Differentially Localized Incorporation of Amino Acids in relation to Epidermal Keratinization in the Newborn Rat," The Anatomical Record, 1965, pp. 525-536, vol. 152.
Gibbs, Neil K., et al., "Action Spectra For The Trans To Cis Photoisomerisation Of Urocanic Acid In Vitro And In Mouse Skin," Rapid Communication, Photochemistry and Photobiology, 1993, pp. 584-590, vol. 57, No. 3, American Society for Photobiology.
Jansén, C.T., et al., "A Non-invasive Chamber Sampling Technique for HPLC Analysis of Human Epidermal Urocanic Acid Isomers," Short Reports, Acta. Derm. Venereol. (Stockh), 1991, pp. 143-145, 71.
Kammeyer, Arthur, et al., "Suppression of Different Phases of Systemic Contact Hypersensitivity by Urocanic Acid Oxidation Products," Photochemistry and Photobiology, 2004, pp. 72-77, 80, American Society for Photobiology.
Kopple, Joel D. et al., "Evidence that Histidine is an Essential Amino Acid in Normal and Chronically Uremic Man," The Journal of Clinical Investigation, 1975, pp. 881-891, vol. 55.
Krien Paul M., et al., "Evidence for the Existence of a Self-Regulated Enzymatic Process within the Human Stratum Corneum—An Unexpected Role for Urocanic Acid," J. Invest. Dermatol, Sep. 2000, pp. 414-420, vol. 115, No. 3, The Society for Investigative Dermatology, Inc.
Lynley, Alexis M., et al., "The Characterization Of Human Epidermal Filaggrin a Histidine-Rich, Keratin Filament-Aggregating Protein," Biochim. Biophys. Acta. 1983, pp. 28-35, 14: 744, Elsevier Biomedical Press.
Mauro, Theodora, et al., "Barrier recovery is impeded at neutral pH, independent of ionic effects: implications for extracellular lipid processing," Arch. Dermatol. Res., 1998, pp. 215-222, 290, Springer-Verlag.
McLoone, Pauline, et al., "An Action Spectrum for the Production of cis-Urocanic Acid in Human Skin In Vivo," J. Invest. Dermatol., 2005, pp. 1071-1074, 124, The Society for Investigative Dermatology, Inc.

Morison, Warwick, "Phototherapy and Photochemotherapy: An Update," Seminars in Cutaneous Medicine and Surgery, Dec. 1999, pp. 297-306, vol. 18, No. 4, W.B. Saunders Company.
Norval, Mary, et al., "Studies to determine the immunomodulating effects of cis-urocanic acid," Methods, 2002, pp. 63-70, 28, Elsevier Science (USA).
Office Action dated Aug. 9, 2012 (28 pages), U.S. Appl. No. 12/918,701, filed Aug. 20, 2010.
Office Action (Final) dated Dec. 21, 2012 (15 pages), U.S. Appl. No. 12/918,701, filed Aug. 20, 2010.
Office Action dated Nov. 19, 2014 (20 pages), U.S. Appl. No. 12/918,701, filed Aug. 20, 2010.
Office Action (Final) dated May 27, 2015 (12 pages), U.S. Appl. No. 12/918,701, filed Aug. 20, 2010.
Office Action dated Oct. 11, 2016 (25 pages), U.S. Appl. No. 14/950,559, filed Nov. 24, 2015.
Office Action (Final) dated May 1, 2017 (30 pages), U.S. Appl. No. 14/950,559, filed Nov. 24, 2015.
Office Action dated Jan. 2, 2018 (18 pages), U.S. Appl. No. 14/950,559, filed Nov. 24, 2015.
Office Action (Final) dated Aug. 21, 2018 (21 pages), U.S. Appl. No. 14/950,559, filed Nov. 24, 2015.
Office Action (Final) dated May 15, 2019 (25 pages), U.S. Appl. No. 14/950,559, filed Nov. 24, 2015.
Office Action dated Dec. 3, 2019 (15 pages), U.S. Appl. No. 14/950,559, filed Nov. 24, 2015.
Office Action (Final) dated Jun. 11, 2020 (19 pages), U.S. Appl. No. 14/950,559, filed Nov. 24, 2015.
Office Action dated Dec. 23, 2021 (22 pages), U.S. Appl. No. 14/950,559, filed Nov. 24, 2015.
Product information for "Pure L-Histidine 600 Mg," http://www.naturalhealthyconcepts.com/pure-I-histidine-600mg-50-p-montiff.html, Apr. 1, 2002, 1 page, Montiff.
Reilly, Sheryl K., "Dietary Histidine Increases Mouse Skin Urocanic Acid Levels and Enhances UVB-Induced Immune Suppression of Contact Hypersensitivity," Rapid Communication, Photochemistry and Photobiology, 1991, pp. 431-438, vol. 57, No. 3, American Society for Photobiology.
Reynolds, Nick J., et al., "Narrow-band ultraviolet B and broadband ultraviolet A phototherapy in adult atopic eczema: a randomised controlled trial," The Lancet, Jun. 23, 2001, pp. 2012-2016, vol. 357.
Rippke, Frank, et al., "Stratum Corneum pH in Atopic Dermatitis Impact on Skin Barrier Function and Colonization with *Staphylococcus aureus*," Am. J. Clin. Dermatol, 2004, pp. 217-223, vol. 5, No. 4, Adis Data Information BV.
Scott, Ian R. et al., "Histidine-Rich Protein of the Keratohyalin Granules Source of the Free Amino Acids, Urocanic Acid and Pyrrolidone Carboxylic Acid in the Stratum Corneum," Biochimica et Biophysica Acta, 1982, pp. 110-117, vol. 719, Elsevier Biomedical Press.
Schmid-Wendtner M.H., et al., "The pH of the Skin Surface and Its Impact on the Barrier Function," Skin Pharmacol. Physiol, Jul. 19, 2006, pp. 296-302,19, S. Karger AG, Basel.
Schmitt, Jochen, et al., "What are the best outcome measurements for atopic eczema? A systematic review," J. Allergy Clin. Immunol., Dec. 2007, pp. 1389-1398, 120, American Academy of Allergy, Asthma & Immunology.
Steinhoff, Ständer S., et al., "Pathophysiology of pruritus in atopic dermatitis: an overview," Exp. Dermatol., 2002, pp. 12-24, 11, Munksgaard.
Williams, H.C., et al., "The U.K. Working Party's Diagnostic Criteria for Atopic Dermatitis. I. Derivation of a minimum set of discriminators for atopic dermatitis," British Journal of Dermatology, 1994, pp. 383-396, 131.

* cited by examiner

Figure 1

Day 1

Figure 2A

Day 6

Figure 2B

Day 13

Figure 2C

Day 19

Figure 2D

HISTIDINE AND/OR HISTIDINE DERIVATIVE FOR THE TREATMENT OF INFLAMMATORY SKIN DISEASES

CROSS-REFERENCE TO RELATED APPLICATIONS

This application is a continuation of and claims priority to U.S. patent application Ser. No. 14/950,559 filed on Nov. 24, 2015, published as U.S. Patent Application Publication No. 2016/0074365 A1, which is a divisional of and claims priority to U.S. patent application Ser. No. 12/918,701 filed on Aug. 20, 2010, published as U.S. Patent Application Publication No. US2010/0331235 A1, which claims benefit of International Application No. PCT/GB2009/000430 filed Feb. 18, 2009, and all entitled "Histidine and/or Histidine Derivative for the Treatment of Inflammatory Skin Diseases," which, in turn, claims benefit of United Kingdom Application No. 0803054.6 filed on Feb. 20, 2008 and entitled "Medicament," all of which are hereby incorporated herein by reference in their entirety for all purposes.

STATEMENT REGARDING FEDERALLY SPONSORED RESEARCH OR DEVELOPMENT

Not applicable.

BACKGROUND

The present invention relates to histidine and/or a derivative thereof for use in maintaining and/or improving barrier function of the skin of a subject, for example for use in the prevention and/or treatment of skin disorders, particularly inflammatory skin diseases such as atopic dermatitis. The present invention also relates to pharmaceutical compositions and nutritional products comprising histidine and/or a derivative thereof, for example for use in maintaining and/or improving barrier function of the skin of a subject, for example for use in the prevention and/or treatment of skin disorders, particularly inflammatory skin diseases such as atopic dermatitis.

Skin disorders such as inflammatory skin diseases are prevalent in the global population, including in adults, children and infants. For example, atopic dermatitis (also known as atopic eczema) is a chronic inflammatory skin disease that causes the skin of a patient to react easily and abnormally to irritants, food and environmental allergens and to become vulnerable to surface infections caused by bacteria. Atopic dermatitis currently is managed by a combination of prevention, for example through learning what triggers the allergic reactions, and drug therapy. Another form of treatment includes exposure to broad or narrow band ultraviolet radiation, which is believed to have a localised immunomodulatory effect on affected tissues. However, ultraviolet radiation is not without risk, it being implicated in various types of skin cancer.

Another chronic inflammatory skin disease is psoriasis, of which there are several types. The most common type is plaque psoriasis, which causes red scaly patches (psoriatic plaques) to appear on the skin that represent areas of inflammation and excessive skin production. Other types include flexural, guttate, pustular, nail, erythrodermic psoriasis and psoriatic arthritis. Psoriasis currently is managed by drug therapy (such as by topical treatments) and/or by exposure to ultraviolet radiation.

Skin disorders such as chronic inflammatory skin diseases can be debilitating and cause anxiety, loss of quality of life, and depression in sufferers. Such skin disorders often reoccur after conventional treatments, making their long-term management and treatment difficult. Skin disorders, such as chronic inflammatory skin diseases, therefore represent a major problem to sufferers and effective treatments are urgently required.

The causes of inflammatory skin diseases such as atopic dermatitis and psoriasis are not well understood and it is believed that numerous factors are involved. These factors are believed to include defects in the process by which skin cells of patients grow, reproduce and differentiate, as well as immune-mediated processes (i.e. abnormal immune responses). The numerous factors involved make providing an effective treatment difficult and challenging to persons skilled in the art.

Current treatments for skin disorders typically are ineffective, especially in respect to long-term treatment, cause undesired side effects and/or are unsuitable for treating a range of such disorders. Thus, there exists an unmet clinical need to find new and effective treatments for skin disorders, which may be used alone or in combination with current treatments. It would be desirable for such treatments to provide effective prevention and/or treatment of a wide range of skin disorders whilst exhibiting low toxicity and side effects.

BRIEF DESCRIPTION OF THE FIGURES

For a detailed description of the disclosed embodiments, reference will now be made to the accompanying drawings in which.

DETAILED DESCRIPTION OF THE DISCLOSED EMBODIMENTS

The present inventor has provided a novel and effective treatment of skin disorders (particularly of inflammatory skin diseases, especially atopic dermatitis) using histidine and/or derivatives thereof, and novel pharmaceutical compositions and nutritional products that may be used in such treatments. No such pharmaceutical compositions, nutritional products and treatments are known.

US 2006/0204552 discloses a pet foodstuff comprising pantothenic acid, nicotinamide, histidine, inositol and choline. The foodstuff is intended for treating and controlling skin disorders in pets. There is no disclosure in this document of a pharmaceutical composition comprising histidine and/or a derivative thereof.

Dave V K and Anthon B, Acta. Derm. Venereol (Stockh) 1987; 67: 274 discloses a composition comprising 2% L-histidine and 1% hydrocortisone in either aqueous cream BP or white soft paraffin and its topical use in the treatment of psoriasis and nickel-induced dermatitis. There is no disclosure in this document of the use of histidine and/or a derivative thereof to treat atopic dermatitis or of a pharmaceutical composition comprising histidine and/or a derivative thereof formulated for oral administration.

Additionally, nutritional supplements comprising histidine are known, but such supplements are not formulated as pharmaceutical compositions or intended for use in treating skin disorders and maintaining and/or improving barrier function of the skin.

According to the present invention, there is provided histidine and/or a derivative thereof for use in maintaining and/or improving barrier function of the skin of a subject. There is also provided the use of histidine and/or a derivative thereof in the manufacture of a medicament for use in maintaining and/or improving barrier function of the skin of a subject.

According to the present invention, there is also provided a method for maintaining and/or improving barrier function of the skin of a subject in need thereof, which method comprises administering to said subject a therapeutically effective amount of histidine and/or a derivative thereof.

References to maintaining the barrier function of the skin are intended to relate to maintaining barrier function of the skin as found in a healthy subject, i.e. substantially "normal" barrier function of the skin. References to improving barrier function of the skin are intended to relate to improving the barrier function such that it approaches or reaches that found in a healthy subject. Barrier function of the skin is critical to preservation of the moisture content of the skin and the ability of the skin to resist ingress of microorganisms, viruses, allergens, toxins, irritants and other exogenous pathogenic factors. Abnormal skin barrier function results in increased trans-epidermal water loss (TEWL) and increased ingress of microorganisms, viruses, allergens, toxins, irritants and other exogenous pathogenic factors.

References to the manufacture of medicaments relate to medicaments in any suitable form, including for example medicaments in the form of pharmaceutical compositions as described herein.

According to another aspect of the present invention, there is provided histidine and/or a derivative thereof for use in the prevention and/or treatment of a skin disorder in a subject. There is also provided the use of histidine and/or a derivative thereof in the manufacture of a medicament for use in the prevention and/or treatment of a skin disorder in a subject.

According to another aspect of the present invention, there is provided a method for the prevention and/or treatment of a skin disorder in a subject in need thereof, which method comprises administering to said subject a therapeutically effective amount of histidine and/or a derivative thereof.

The skin disorder may be an inflammatory skin disease (particularly a chronic inflammatory skin disease), such as atopic dermatitis, all types of psoriasis (including plaque flexural, guttate, pustular, nail, photosensitive, erythrodermic psoriasis and psoriatic arthritis), acne, ichthyosis, contact dermatitis, eczema, photodermatoses and dry skin disorders. In particular, the skin disorder may be an inflammatory skin disease (particularly a chronic inflammatory skin disease), such as atopic dermatitis, acne, ichthyosis, contact dermatitis, eczema, photodermatoses and dry skin disorders. More particularly the skin disorder may be an inflammatory skin disease (particularly a chronic inflammatory skin disease), such as atopic dermatitis, acne, ichthyosis, contact dermatitis, photodermatoses and dry skin disorders. More particularly, the skin disorder may be atopic dermatitis. References herein to psoriasis refer to all types of psoriasis unless otherwise specified.

According to another aspect of the present invention, there is provided histidine and/or a derivative thereof for use in the prevention and/or treatment of an inflammatory skin disease (particularly a chronic inflammatory skin disease) in a subject. There is also provided the use of histidine and/or a derivative thereof in the manufacture of a medicament for use in the prevention and/or treatment of an inflammatory skin disease (particularly a chronic inflammatory skin disease) in a subject.

According to another aspect of the present invention, there is provided a method for the prevention and/or treatment of an inflammatory skin disease (particularly a chronic inflammatory skin disease) in a subject in need thereof, which method comprises administering to said subject a therapeutically effective amount of histidine and/or a derivative thereof.

Thus, according to the present invention, there is provided histidine and/or a derivative thereof for use in the prevention and/or treatment of an inflammatory skin disease (particularly a chronic inflammatory skin disease) in a subject, wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis). There is also provided the use of histidine and/or a derivative thereof in the manufacture of a medicament for use in the prevention and/or treatment of an inflammatory skin disease (particularly a chronic inflammatory skin disease) in a subject, wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis).

According to another aspect of the present invention, there is provided a method for the prevention and/or treatment of an inflammatory skin disease (particularly a chronic inflammatory skin disease) in a subject in need thereof, which method comprises administering to said subject a therapeutically effective amount of histidine and/or a derivative thereof, wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis).

Further, according to the present invention, there is provided histidine and/or a derivative thereof for use in the prevention and/or treatment of atopic dermatitis in a subject. There is also provided the use of histidine and/or a derivative thereof in the manufacture of a medicament for use in the prevention and/or treatment of atopic dermatitis in a subject.

According to another aspect of the present invention, there is provided a method for the prevention and/or treatment of atopic dermatitis in a subject in need thereof, which method comprises administering to said subject a therapeutically effective amount of histidine and/or a derivative thereof.

The inventors have appreciated that in skin disorders, such as inflammatory skin diseases (for example atopic dermatitis), skin barrier function is impaired and impaired skin barrier function may be a cause of the disorder. The inventors therefore have appreciated that it is desirable to maintain and/or improve barrier function of the skin.

Skin barrier function is controlled by many factors, including the proteins present and the environment in which they reside (for example the pH). The inventors have further appreciated that one cause of impaired skin barrier function may be due to defective filaggrin. Filaggrin (i.e. filaggrin-aggregating protein) is a structural protein that is intimately involved in terminal differentiation of keratinocytes (the major cell type of the epidermis) and skin barrier function. Filaggrin binds to keratins to produce flattened squames, which play an important part in epidermal barrier function (see Lynley A M and Dale B A, *Biochim. Biophys. Acta.* 1983; 14: 744: 28-35).

Figure 1:
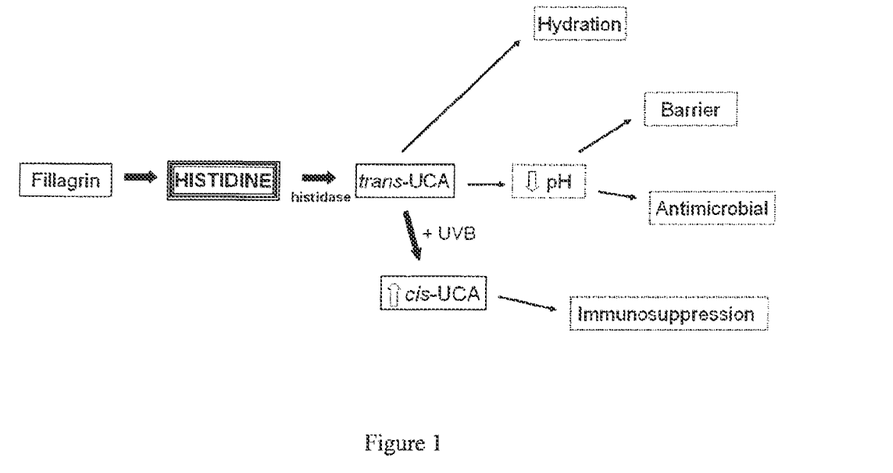
FIG. 1 illustrates a filaggrin metabolic pathway.

Furthermore, filaggrin (also known as 'histidine-rich protein') is broken down by proteinases to release a large amount of constituent histidine residues. The histidine residues are then deaminated by histidase to form trans-urocanic acid (trans-UCA). The filaggrin metabolic pathway is shown in FIG. 1. Trans-UCA is the major proton-donating molecule in the stratum corneum (see Krien P M and Kermici M, *J. Invest. Dermatol.* 2000; 115: 414-20). In normal skin many proteins involved in barrier formation are pH dependent and are only active in the UCA-created acidic environment of the upper epidermis/stratum corneum (see Schmid-Wendtner M H and Korting H C, *Skin Pharmacol. Physiol.* 2006: 19:296-302). In addition to maintaining this homeostasis, the lowered pH of the stratum corneum directly inhibits microbial infection and growth (see Rippke et al, *Am. J. Clin. Dermatol.* 2004; 5:217-23). The inventors have appreciated that defective filaggrin may result in reduced amino acid content, especially reduced levels of histidine in the stratum corneum, which in turn may lead to reduced levels of trails-UCA and an abnormally high pH. A higher than optimum pH in the stratum corneum is believed to reduce pH dependent lipid processing enzymes (for example β-glucocerebrosidase) and compromise barrier function and repair (see Mauro et al, *Arch. Dermatol. Res.* 1998; 290: 215-22 and Rippke et al, *Am. J. Clin. Dermatol.* 2004; 5:217-23).

Thus, the present invention is believed to address the problem of defective filaggrin in patients suffering from the skin disorders. Without wishing to be bound by any theory, it is believed that the histidine and/or the derivative thereof as the active ingredient in the uses, pharmaceutical compositions and nutritional products of the present invention potentially may compensate for defective filaggrin and for associated defects in barrier function in patients with skin disorders, so as to increase levels of histidine and trans-UCA in the skin of patients. This in turn may restore the pH required by the cells to maintain and restore barrier function of the dermis, leading to the prevention and/or treatment of skin disorders. However, the histidine and/or derivative thereof may of course act by means of another route to achieve the result of maintaining and restoring barrier function of the dermis, leading to the prevention and/or treatment of skin disorders. There currently exists no means to prevent and/or treat skin disorders such as atopic dermatitis that addresses the problem of defective filaggrin in patients suffering from these disorders.

Moreover, histidine and derivatives thereof exhibit low or no toxicity to a subject (such as animals, especially warm-blooded animals such as man) and no reported side effects at conventional doses. Such properties of histidine and derivatives thereof as the active ingredient provide advantages in use, including easy access to patients, improving patient compliance and increasing the potential usage of the active ingredients in wide patient populations and for longer treatment regimes, for example compared to alternative medicaments currently in use. Moreover, histidine and derivatives thereof are expected to be useful in treating the entire body surface of patients and to be effective against a wide range of skin disorders (especially inflammatory skin diseases). Histidine and derivatives thereof may also have some use in reducing or preventing hypersensitivity of the skin to allergens such as metals (for example nickel).

The histidine and/or the derivative thereof may be used as described herein, for example for maintaining and/or improving barrier function of the skin of a subject and/or in the prevention and/or treatment of a skin disorder (such as an inflammatory skin disease, especially atopic dermatitis) in any suitable form, for example as discussed herein. For example the histidine and/or the derivative thereof may be used in a form for oral or topical administration.

The histidine and/or the derivative thereof may be used as a sole therapy or in combination with a conventional therapy for the prevention and/or treatment of skin disorders (such as inflammatory skin diseases). Suitable such conventional therapies include treatment with steroids (for example steroids for topical administration) and/or with suitable lipids and/or with phototherapy. For example, the histidine and/or the derivative thereof may be used in combination with phototherapy, and optionally a further conventional therapy, for the prevention and/or treatment of skin disorders such as inflammatory skin diseases (especially atopic dermatitis).

According to another aspect of the invention, there is provided histidine and/or a derivative thereof for use in combination with a conventional therapy for the prevention and/or treatment of skin disorders such as inflammatory skin diseases. For example, there may be provided histidine and/or a derivative thereof for use in maintaining and/or improving barrier function of the skin of a subject and/or for preventing and/or treating skin disorders such as inflammatory skin diseases as discussed herein (particularly atopic dermatitis), wherein the histidine and/or the derivative thereof is for use in combination a conventional therapy for the prevention and/or treatment of skin disorders such as inflammatory skin diseases (especially atopic dermatitis).

According to another aspect of the invention, there is provided histidine and/or a derivative thereof for use in combination with phototherapy. For example, there may be provided histidine and/or a derivative thereof for use in maintaining and/or improving barrier function of the skin of a subject and/or for preventing and/or treating skin disorders such as inflammatory skin diseases as discussed herein (particularly atopic dermatitis), wherein the histidine and/or the derivative thereof is for use in combination with phototherapy.

According to another aspect of the present invention, there is provided histidine and/or a derivative thereof for use in maintaining and/or improving barrier function of the skin of a subject, wherein the histidine and/or the derivative thereof is for use in combination with phototherapy. There is also provided the use of histidine and/or a derivative thereof in the manufacture of a medicament for use in maintaining and/or improving barrier function of the skin of a subject, wherein the histidine and/or the derivative thereof is for use in combination with phototherapy.

There is also provided a method for maintaining and/or improving barrier function of the skin of a subject in need thereof, which method comprises administering to said subject a therapeutically effective amount of histidine and/or a derivative thereof prior to and/or during and/or after (particularly prior to and/or during) phototherapy treatment.

According to another aspect of the present invention, there is provided histidine and/or a derivative thereof for use in the prevention and/or treatment of a skin disorder in a subject, wherein the histidine and/or the derivative thereof is for use in combination with phototherapy. There is also provided the use of histidine and/or a derivative thereof in the manufacture of a medicament for use in the prevention and/or treatment of a skin disorder in a subject, wherein the histidine and/or the derivative thereof is for use in combination with phototherapy.

There is also provided a method for the prevention and/or treatment of a skin disorder in a subject in need thereof, which method comprises administering to said subject a therapeutically effective amount of histidine and/or a derivative thereof prior to and/or during and/or after (particularly prior to and/or during) phototherapy treatment.

According to another aspect of the invention, there is provided histidine and/or a derivative thereof for use in the prevention and/or treatment of an inflammatory skin disease (particularly a chronic inflammatory skin disease) in a subject, wherein the histidine and/or the derivative thereof is for use in combination with phototherapy. There is also provided the use of histidine and/or a derivative thereof in the manufacture of a medicament for use in the prevention and/or treatment of an inflammatory skin disease (particularly a chronic inflammatory skin disease) in a subject, wherein the histidine and/or the derivative thereof is for use in combination with phototherapy.

According to another aspect of the present invention, there is provided a method for the prevention and/or treatment of an inflammatory skin disease (particularly a chronic inflammatory skin disease) in a subject in need thereof, which method comprises administering to said subject a therapeutically effective amount of histidine and/or a derivative thereof prior to and/or during and/or after (particularly prior to and/or during) phototherapy treatment.

Thus, according to the present invention, there is provided histidine and/or a derivative thereof for use in the prevention and/or treatment of an inflammatory skin disease (particularly a chronic inflammatory skin disease) in a subject, wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis) and wherein the histidine and/or the derivative thereof is for use in combination with phototherapy.

There is also provided the use of histidine and/or a derivative thereof in the manufacture of a medicament for use in the prevention and/or treatment of an inflammatory skin disease (particularly a chronic inflammatory skin disease) in a subject, wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis) and wherein the histidine and/or the derivative thereof is for use in combination with phototherapy.

According to another aspect of the present invention, there is provided a method for the prevention and/or treatment of an inflammatory skin disease (particularly a chronic inflammatory skin disease) in a subject in need thereof, which method comprises administering to said subject a therapeutically effective amount of histidine and/or a derivative thereof prior to and/or during and/or after (particularly prior to and/or during) phototherapy treatment, wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis).

Further, according to the present invention, there is provided histidine and/or a derivative thereof for use in the prevention and/or treatment of atopic dermatitis in a subject, wherein the histidine and/or the derivative thereof is for use in combination with phototherapy. There is also provided the use of histidine and/or a derivative thereof in the manufacture of a medicament for use in the prevention and/or treatment of atopic dermatitis in a subject, wherein the histidine and/or the derivative thereof is for use in combination with phototherapy.

According to another aspect of the present invention, there is provided a method for the prevention and/or treatment of atopic dermatitis in a subject in need thereof, which method comprises administering to said subject a therapeutically effective amount of histidine and/or a derivative thereof prior to and/or during and/or after (particularly prior to and/or during) phototherapy treatment.

Any suitable phototherapy may be used in these aspects of the invention. For example, the phototherapy may involve the exposure of the subject to ultraviolet radiation, especially narrow-band ultraviolet-B radiation (for example known as Philips TL-01 phototherapy). References herein to phototherapy include photochemotherapy (for example Psoralen plus UVA photochemotherapy, known as PUVA). Localised or whole-body phototherapy may be used. The subject may be treated with the phototherapy prior to, during and/or after the treatment with histidine and/or a derivative thereof.

The histidine and/or a derivative thereof may be used in combination with a conventional therapy, such as phototherapy (including photochemotherapy), in any suitable form, for example as discussed herein. For example the histidine and/or derivative thereof may be used in a form for oral or topical administration. An oral dosage form may be used (for example a pharmaceutical composition or nutritional product for oral administration), which oral dosage form may be administered to the subject at a suitable time prior to, during and/or after (particularly prior to) the phototherapy. A topical dosage form may be used (for example a pharmaceutical composition for topical administration), which may be applied to the skin of the subject at a suitable time prior to, during and/or after (particularly prior to) the phototherapy.

On exposure of the skin of a subject to ultra-violet radiation, trans-UCA undergoes wavelength dependent photoisomerisation to its cis-isomeric form; cis-UCA (see Gibbs et al, *J. Rapid Communication, Photochem. Photobiol.* 1993; 57: 584-590 and McLoone et al, *J. Invest. Dermatol.* 2005; 124: 1071-4). Trans-UCA is understood to be important in UVB-induced photoimmunosuppression (see De Fabo E C and Noonan F P, *J. Exp. Med.* 1983; 157, 84-98) and it has been shown that cis-UCA can suppress both the sensitisation and elicitation phases of contact and delayed type hypersensitivity, resistance to infectious diseases, skin and other allograft rejection and graft-versus-host disease (see Norval M and El-Ghorr A A, *Methods* 2002; 28: 63-70 and Kammeyer A et al, *Photochem. Photobiol.* 2004; 80:72-7). Thus, both trans-UCA and cis-UCA are believed to be useful in treating skin disorders (for example inflammatory skin diseases as discussed herein). As discussed above, the inventors have appreciated that providing histidine and/or a derivative thereof to a patient in need of such treatment potentially may help to increase levels of trans-UCA in the skin, which is believed to restore the desired pH and barrier function so as to prevent and/or treat skin disorders. The inventors have further appreciated that by administering the histidine and/or the derivative thereof in combination with phototherapy, levels of trans- and cis-UCA may be further increased, such that prevention and/or treatment is further improved. In other words, the pharmaceutical compositions, nutritional products and uses of the present invention are believed to improve response to phototherapy. This is turn may decrease phototherapy times, improve patient compliance and reduce treatment costs.

The histidine and/or derivative thereof may be provided for the uses discussed above in any suitable form, including for example in a form for administration alone and/or formulated as a pharmaceutical composition or nutritional product (or nutraceutical). Thus, there is further provided histidine and/or a derivative thereof for use in maintaining and/or improving barrier function of the skin of a subject and/or for the prevention and/or treatment of skin disorders (such as inflammatory skin diseases as discussed herein and particularly atopic dermatitis) in the form of a pharmaceutical composition (for example a pharmaceutical composition as described herein). There is further provided a pharmaceutical composition comprising histidine and/or a derivative thereof (for example a pharmaceutical composition as described herein) for any use as described herein.

There is further provided histidine and/or a derivative thereof for use in maintaining and/or improving barrier function of the skin of a subject and/or for the prevention and/or treatment of skin disorders (such as inflammatory skin diseases as discussed herein and particularly atopic dermatitis) in the form of a nutritional product (for example a nutritional product (or nutraceutical) as described herein). There is further provided a nutritional product comprising histidine and/or a derivative thereof (for example a nutritional product (or nutraceutical) as described herein) for any use as described herein.

According to another aspect of the present invention, there is provided a pharmaceutical composition comprising a therapeutically effective amount of histidine and/or a derivative thereof as the active ingredient in combination with a pharmaceutically-acceptable diluent or carrier.

By a pharmaceutical composition we mean a composition including an active ingredient that is suitable for administration to a subject so as to treat and/or prevent a medical disorder or condition. An active ingredient is an agent that is effective against a disorder, such that when it is administered to a subject suffering from the disorder it causes reduction, remission, or regression of the disorder. In order words, the active ingredient is effective to treat a disorder by causing reduction, remission, or regression of the disorder. An active ingredient is also typically effective in the prevention of a disorder upon administration to a subject, i.e. so as to prevent and/or delay onset of the disorder.

The pharmaceutical composition of the invention comprises histidine and/or a derivative thereof as the active ingredient (i.e. such that when the histidine and/or the derivative thereof is administered to a subject suffering from a disorder, for example as described herein, it causes prevention, reduction, remission and/or regression of the disorder). In particular, there is provided a pharmaceutical composition in which the histidine and/or the derivative thereof is the only active ingredient. Thus, there is further provided a pharmaceutical composition comprising a therapeutically effective amount of histidine and/or a derivative thereof as the active ingredient in combination with a pharmaceutically-acceptable diluent or carrier, wherein the histidine and/or the derivative thereof is the only active ingredient in the pharmaceutical composition.

According to another aspect of the present invention, there is provided a pharmaceutical composition consisting of a therapeutically effective amount of histidine and/or a derivative thereof as the active ingredient and a pharmaceutically-acceptable diluent or carrier.

The inventors have unexpectedly provided a pharmaceutical composition that may be used to deliver a therapeutically effective amount of histidine and/or a derivative thereof to the skin. It would not have been obvious to a person skilled in the art how to provide such a pharmaceutical composition. The skilled person may have expected the oral administration of such an active ingredient to increase histidine levels in the blood stream but he would not have expected this to result in sufficient levels in the skin to treat skin disorders as described herein. Similarly, it would have been unexpected to the skilled person that the topical administration of histidine and/or a derivative thereof would have enabled the active ingredient to cross the intact skin-barrier so as to be present at levels sufficient for maintaining and/or improving barrier function of the skin and treating skin disorders. Additionally, the skilled person would not have expected the administration of histidine and/or a derivative thereof (for example orally or topically) to provide a mechanism of controlling the skin homeostasis (for example pH) so as to maintain it within the narrow physiological range in which barrier function and repair is optimised.

Furthermore, it would have been counterintuitive to include histidine and/or a derivative thereof in a pharmaceutical composition intended for use in the prevention or treatment of a skin disorder such as atopic dermatitis. The skilled person would have expected the histidine and/or the derivative thereof potentially to produce or aggravate an allergic reaction because he would have understood that histidine can be broken down to histamine, which is believed to be a major mediator of allergenic responses and to exacerbate the itch associated with many skin disorders such as atopic dermatitis (see Stander S and Steinhoff M., *Exp Dermatol.* 2002; 11: 12-24.)

Additionally, as histidine is a hydrophobic amino acid, the administration of histidine to the skin would not have been expected to prevent trans epidermal water loss. Moreover, it would have been surprising to the skilled person that histidine and/or a derivative thereof would have acted alone as an active ingredient in preventing or treating skin disorders. As discussed above, known products such as the pet foodstuff disclosed in US 2006/0204552 including histidine comprise the histidine in combination with other active ingredients.

Any suitable pharmaceutically-acceptable diluent or carrier may be included in the pharmaceutical compositions of the invention, which diluents or carriers would be well known to persons skilled in the art. The particular diluents or carriers selected depend on various factors, including the dosage of the active ingredient, the mode of administration of the composition and the stability of the active ingredient. The pharmaceutically-acceptable diluent or carrier should be selected so as to deliver a sufficient amount of the active ingredient to the skin.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene, isopropyl myristate or water. Similarly, the carrier or diluent may include any sustained release material known in the art, such as glycerol monostearate or glycerol distearate, alone or mixed with wax.

The pharmaceutical compositions of the invention may be formulated for administration by any convenient route. For example, the pharmaceutical compositions may be in a form suitable for oral administration (for example as tablets, lozenges, hard or soft capsules, aqueous or oily suspensions, emulsions, dispersible powders or granules, syrups or elixirs), for topical administration (for example as creams, ointments, gels, or aqueous or oily solutions or suspensions, or by transdermal delivery), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

According to another aspect of the invention, there is provided a pharmaceutical composition comprising a therapeutically effective amount of histidine and/or a derivative thereof as the active ingredient in combination with a pharmaceutically-acceptable diluent or carrier, wherein the pharmaceutical composition is formulated for oral administration. Such a pharmaceutical composition formulated for oral administration may include histidine and/or the derivative thereof as the only active ingredient in the pharmaceutical composition, as discussed above.

It will be appreciated that the preferred route of administration will depend on the general condition and age of the subject to be treated, the nature of the disorder to be treated and the active ingredient chosen.

Pharmaceutical compositions for oral administration may be in a solid dosage form such as capsules, tablets, dragees, pills, lozenges, powders and granules. Solid dosage forms can include one or more substances which may also act as flavoring agents, lubricants, solubilizers, suspending agents, fillers, glidants, compression aids, binders or tablet-disintegrating agents. In powders, the vehicle is a finely divided solid which is in admixture with the active ingredient. In tablets, the active ingredient is mixed with a vehicle having the necessary compression properties in suitable proportions and compacted in the shape and size desired. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Where appropriate, solid dosage forms can be prepared with coatings such as enteric coatings or they can be formulated so as to provide controlled release of the active ingredient such as sustained or prolonged release or bolus application according to the methods well known in the art.

Pharmaceutical compositions for oral administration may alternatively be in a liquid form. A liquid carrier may be in the form of solutions, suspensions, emulsions, syrups, elixirs and pressurized compositions. The active ingredient can be dissolved or suspended in a pharmaceutically-acceptable liquid vehicle such as water (optionally flavoured), an organic solvent, a mixture of both or pharmaceutically-acceptable oils or fats. The liquid vehicle can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid vehicles for oral administration include water (partially containing additives as above, for example cellulose derivatives, preferably sodium carboxymethyl cellulose solution), alcohols (including monohydric alcohols and polyhydric alcohols, for example glycols) and their derivatives, and oils (for example fractionated coconut oil and arachis oil).

The pharmaceutical compositions of the invention can be presented in the form of unit dosage forms containing a defined amount of the active ingredient. Such unit dosage forms can be selected so as to achieve a desired level of biological activity.

In one aspect, the pharmaceutical composition of the present invention may be formulated for oral administration, for example as a discrete unit in the form of a tablet or capsule each containing a predetermined amount of the active ingredient and a suitable pharmaceutically-acceptable carrier or diluent.

The histidine and/or the derivative thereof may be formulated as a powder, granule or semisolid for incorporation into capsules. For presentation in the form of a semisolid, the histidine and/or the derivative thereof may be dissolved or suspended in a viscous liquid or semisolid vehicle such as a polyethylene glycol, or a liquid carrier such as a glycol (for example propylene glycol or glycerol) or a vegetable or fish oil (for example an oil selected from olive oil, sunflower oil, safflower oil, evening primrose oil, soya oil, cod liver oil, herring oil, etc). This may then be filled into capsules of either the hard gelatine or soft gelatine type or made from hard or soft gelatine equivalents, soft gelatine or gelatine-equivalent capsules being preferred for viscous liquid or semisolid fillings.

The histidine and/or the derivative thereof may be formulated as a powder for dissolving or suspending in a suitable liquid carrier.

Powder forms of the histidine and/or the derivative thereof may be prepared by any suitable method, including freeze-drying or spray drying, and typically are available from commercially sources, for example synthesised according to desired Good Manufacturing Practice (GMP).

Powder forms of the histidine and/or the derivative thereof may be incorporated into slow-release capsules or devices which may be ingested and are able to release the histidine and/or the derivative thereof into the intestines over a long period of time.

The histidine and/or the derivative thereof may also be microencapsulated. For instance encapsulation may be by calcium-alginate gel capsule formation. Kappa-carrageenan, gellan gum, gelatin and starch may be used as excipients for micro-encapsulation.

In another aspect, the pharmaceutical composition of the present invention may be formulated for topical administration, including for administration directly to the skin of a subject, for example at an area requiring treatment. Such a pharmaceutical composition formulated for topical administration may include histidine and/or the derivative thereof as the only active ingredient in the pharmaceutical composition, as discussed above.

Pharmaceutical compositions for topical administration may for example be in the form of solutions, creams, ointments, jellies, gels, sprays, foams, powders, liposomes, or aqueous or oily solutions or suspensions. Suitable diluents and carriers include, for example, peanut oil, water, ethyl cocoate, octyl cocoate, polyoxyethylenated hydrogenated caster oil, liquid paraffin, isopropanol, glycerol, propylene glycol, paraffin, celluloses, parabens, stearyl alcohol, polyethylene glycol, isopropyl myristate and phenoxyethanol.

In the case of topical application to the scalp, the pharmaceutical composition may be formulated as a shampoo. In the case of topical application to the skin, the pharmaceutical composition may be formulated as an additive to wash water (for example in the form of a bath or shower gel or cream), such as to bath water etc. Such pharmaceutical compositions for topical administration may include diluents or carriers that are also suitable for use in cosmetics.

Pharmaceutical compositions for topical administration by application to the skin may include moisturizers, and sun tan lotions and creams.

A pharmaceutical composition for topical administration may be provided in a suitable container, such as a pipette, for direct administration in one or two spots to the skin, for example for administration to a pet such as a dog or cat. For example, a pipette may be provided with a snap-off top and containing a single dosage of the active ingredient, such that direct administration of the whole contents of the pipette in one or two spots to the skin provides a desired dosage of the active ingredient.

In the case of pharmaceutical compositions for topical administration by application to the skin, the diluent or carrier should be selected so as to assist the transport of the active ingredient across the skin barrier and may need to be one capable of crossing the keratinous layer of the skin. Examples of suitable diluents/carriers for this purpose include dimethyl sulfoxide and acetic acid. Many methods are known for preparation of pharmaceutical compositions for topical application. For example, the active ingredient may be mixed with known carrier materials as discussed herein.

Suitable pharmaceutical compositions for topical administration may also include a known chemical absorption promoter. Examples of absorption promoters are for example dimethylacetamide (U.S. Pat. No. 3,472,931), trichloroethanol or trifluoroethanol (U.S. Pat. No. 3,891, 757) certain alcohols and mixtures thereof (GB-1,001,949). A carrier material for topical application to unbroken skin is also described in GB-1,464,975, which discloses a carrier material consisting of a solvent comprising 40 to 70% (v/v) isopropanol and 0 to 60% (v/v) glycerol, the balance, if any, being an inert constituent of a diluent not exceeding 40% of the total volume of solvent.

Alternatively, the skilled person will appreciate that topical administration may be achieved by means of localised injection, for example intra-dermal injection.

Alternatively, the skilled person will appreciate that topical administration may be achieved by means of diffusion from or through a suitable material to the skin, i.e. wherein the active ingredient is releasably contained in or applied to the material for release to the skin upon contact therewith. For example, suitable materials may be provided in the form of a garment, such as gloves, socks or tights, whereby contact with the skin is achieved when the subject wears the garment. An example of a suitable such garment is disclosed, for example, in U.S. Pat. No. 5,614,202.

The active ingredient is present in the pharmaceutical composition in a therapeutically effective amount. A "therapeutically effective amount" is any amount of the active ingredient (for example as contained in the pharmaceutical composition as described herein) which, when administered to a subject suffering from a disorder against which the active ingredient is effective, causes prevention, reduction, remission and/or regression of the disorder.

The therapeutically effective amount of active ingredient that is combined with the pharmaceutically-acceptable diluent or carrier to produce a single dosage form will necessarily vary depending upon the nature and severity of the disorder (such as a skin disorder) treated, the particular patient treated and the particular route of administration, according to well known principles of medicine. For example, a composition formulated for oral administration to man will generally contain from about 0.5 mg to 7 g, such as from about 0.1 g to 7 g of active ingredient (more suitably from 1 g to 7 g, for example from 2.5 g to 5 g) which may be compounded with an appropriate and convenient amount of diluent/carrier which may vary from about 5 to about 98 percent by weight of the total composition.

Typically, unit dosage forms for oral administration, such as tablets and capsules, will contain from about 0.5 mg to 1 g (for example from about 0.5 mg to 0.5 g) of histidine and/or a derivative thereof as the active ingredient. For example, unit dosage forms such as tablets and capsules for oral administration may contain from about 0.2 g to 1 g (for example from about 0.2 g to 0.5 g) of histidine and/or a derivative thereof as the active ingredient.

Typically, compositions for topical administration (such as a cream) will contain from about 0.5 to 80%, more particularly from about 0.5 to 50%, even more particularly from about 1 to 25% by weight of the total composition of histidine and/or a derivative thereof as the active ingredient.

The pharmaceutical compositions of the invention may be obtained by conventional procedures using conventional pharmaceutical diluents or carriers, well known in the art.

The pharmaceutical composition of the invention may be provided for any of the uses as described herein, for example for use in maintaining and/or improving barrier function of the skin of a subject as discussed herein. The pharmaceutical composition of the invention may be provided for the prevention and/or treatment of a skin disorder (such as an inflammatory skin disease, especially atopic dermatitis) in a subject as discussed herein.

According to the present invention, there is also provided a pharmaceutical composition use in maintaining and/or improving barrier function of the skin of a subject, wherein the pharmaceutical composition comprises a therapeutically effective amount of histidine and/or a derivative thereof as the active ingredient. There is also provided the use of histidine and/or a derivative thereof in the manufacture of a pharmaceutical composition for use in maintaining and/or improving barrier function of the skin of a subject.

According to the present invention, there is also provided a method for maintaining and/or improving barrier function of the skin of a subject in need thereof, which method comprises administering to said subject a therapeutically effective amount of a pharmaceutical composition comprising a therapeutically effective amount of histidine and/or a derivative thereof as the active ingredient.

According to another aspect of the present invention, there is provided a pharmaceutical composition for use in the prevention and/or treatment of a skin disorder in a subject, wherein the pharmaceutical composition comprises a therapeutically effective amount of histidine and/or a derivative thereof as the active ingredient. There is also provided the use of histidine and/or a derivative thereof in the manufacture of a pharmaceutical composition for use in the prevention and/or treatment of a skin disorder in a subject.

According to the present invention, there is also provided a method for preventing and/or treating a skin disorder in a subject in need thereof, which method comprises administering to said subject a therapeutically effective amount of a pharmaceutical composition comprising a therapeutically effective amount of histidine and/or a derivative thereof as the active ingredient.

According to another aspect of the present invention, there is provided a pharmaceutical composition for use in the prevention and/or treatment of an inflammatory skin disease (particularly a chronic inflammatory skin disease) in a subject, wherein the pharmaceutical composition comprises a therapeutically effective amount of histidine and/or a derivative thereof as the active ingredient. There is also provided the use of histidine and/or a derivative thereof in the manufacture of a pharmaceutical composition for use in the prevention and/or treatment of an inflammatory skin disease (particularly a chronic inflammatory skin disease) in a subject.

According to the present invention, there is also provided a method for preventing and/or treating an inflammatory skin disease (particularly a chronic inflammatory skin disease) in a subject in need thereof, which method comprises administering to said subject a therapeutically effective amount of a pharmaceutical composition comprising a therapeutically effective amount of histidine and/or a derivative thereof as the active ingredient.

According to another aspect of the present invention, there is provided a pharmaceutical composition for use in the prevention and/or treatment of an inflammatory skin disease (particularly a chronic inflammatory skin disease) in a subject, wherein the pharmaceutical composition comprises a therapeutically effective amount of histidine and/or a derivative thereof as the active ingredient, and wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis). There is also provided the use of histidine and/or a derivative thereof in the manufacture of a pharmaceutical composition for use in the prevention and/or treatment of an inflammatory skin disease (particularly a chronic inflammatory skin disease) in a subject, wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis).

According to the present invention, there is also provided a method for preventing and/or treating an inflammatory skin disease (particularly a chronic inflammatory skin disease) in a subject in need thereof, which method comprises administering to said subject a therapeutically effective amount of a pharmaceutical composition comprising a therapeutically effective amount of histidine and/or a derivative thereof as the active ingredient, wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis).

According to another aspect of the present invention, there is provided a pharmaceutical composition for use in the prevention and/or treatment of atopic dermatitis in a subject, wherein the pharmaceutical composition comprises a therapeutically effective amount of histidine and/or a derivative thereof as the active ingredient. There is also provided the use of histidine and/or a derivative thereof in the manufacture of a pharmaceutical composition for use in the prevention and/or treatment of atopic dermatitis in a subject.

According to the present invention, there is also provided a method for preventing and/or treating atopic dermatitis in a subject in need thereof, which method comprises administering to said subject a therapeutically effective amount of a pharmaceutical composition comprising a therapeutically effective amount of histidine and/or a derivative thereof as the active ingredient.

The histidine and/or the derivative thereof as described herein may be formulated for administration to a subject as a nutritional product or nutraceutical. Such products may be used as staple foods as well as under circumstances where there may be a clinical need. For example, the product may be used as a pet foodstuff.

Accordingly, there is provided a nutritional product (or nutraceutical) comprising a therapeutically effective amount of histidine and/or a derivative thereof as the active ingredient. In particular, in the nutritional product (or nutraceutical) of the invention, the histidine and/or the derivative thereof may be the only active ingredient.

According to one aspect of the invention, there is provided a nutritional product (or nutraceutical) comprising a therapeutically effective amount of histidine and/or a derivative thereof as the active ingredient, wherein the histidine and/or the derivative thereof is the only active ingredient in the nutritional product (or nutraceutical).

According to another aspect of the invention, there is provided a nutritional product (or nutraceutical) consisting of a therapeutically effective amount of histidine and/or a derivative thereof as the active ingredient and a foodstuff.

The nutritional product (or nutraceutical) of the invention may be provided for any of the uses as described herein, for example for use in maintaining and/or improving barrier function of the skin of a subject as discussed herein. The nutritional product (or nutraceutical) of the invention may be provided for the prevention and/or treatment of a skin disorder (such as an inflammatory skin disease, especially atopic dermatitis) in a subject as discussed herein According to the present invention, there is also provided a nutritional product (or nutraceutical) for use in maintaining and/or improving barrier function of the skin of a subject, wherein the nutritional product comprises a therapeutically effective amount of histidine and/or a derivative thereof as the active ingredient. There is also provided the use of histidine and/or a derivative thereof in the manufacture of a nutritional product (or nutraceutical) for use in maintaining and/or improving barrier function of the skin of a subject.

According to the present invention, there is also provided a method for maintaining and/or improving barrier function of the skin of a subject in need thereof, which method comprises administering to said subject a therapeutically effective amount of a nutritional product (or nutraceutical) comprising a therapeutically effective amount of histidine and/or a derivative thereof as the active ingredient.

According to another aspect of the present invention, there is provided a nutritional product (or nutraceutical) for use in the prevention and/or treatment of a skin disorder in a subject, wherein the nutritional product comprises a therapeutically effective amount of histidine and/or a derivative thereof as the active ingredient. There is also provided the use of histidine and/or a derivative thereof in the manufacture of a nutritional product (or nutraceutical) for use in the prevention and/or treatment of a skin disorder in a subject.

According to the present invention, there is also provided a method for preventing and/or treating a skin disorder in a subject in need thereof, which method comprises administering to said subject a therapeutically effective amount of a nutritional product (or nutraceutical) comprising a therapeutically effective amount of histidine and/or a derivative thereof as the active ingredient.

According to another aspect of the present invention, there is provided a nutritional product (or nutraceutical) for use in the prevention and/or treatment of an inflammatory skin disease (particularly a chronic inflammatory skin disease) in a subject, wherein the nutritional product comprises a therapeutically effective amount of histidine and/or a derivative thereof as the active ingredient. There is also provided the use of histidine and/or a derivative thereof in the manufacture of a nutritional product (or nutraceutical) for use in the prevention and/or treatment of an inflammatory skin disease (particularly a chronic inflammatory skin disease) in a subject.

According to the present invention, there is also provided a method for preventing and/or treating an inflammatory skin disease (particularly a chronic inflammatory skin disease) in a subject in need thereof, which method comprises administering to said subject a therapeutically effective amount of a nutritional product (or nutraceutical) comprising a therapeutically effective amount of histidine and/or a derivative thereof as the active ingredient.

According to another aspect of the present invention, there is provided a nutritional product (or nutraceutical) for use in the prevention and/or treatment of an inflammatory skin disease (particularly a chronic inflammatory skin disease) in a subject, wherein the nutritional product comprises a therapeutically effective amount of histidine and/or a derivative thereof as the active ingredient, and wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis). There is also provided the use of histidine and/or a derivative thereof in the manufacture of a nutritional product (or nutraceutical) for use in the prevention and/or treatment of an inflammatory skin disease (particularly a chronic inflammatory skin disease) in a subject, wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis).

According to the present invention, there is also provided a method for preventing and/or treating an inflammatory skin disease (particularly a chronic inflammatory skin disease) in a subject in need thereof, which method comprises administering to said subject a therapeutically effective amount of a nutritional product (or nutraceutical) comprising a therapeutically effective amount of histidine and/or a derivative thereof as the active ingredient, wherein the inflammatory skin disease is selected from one or more of atopic dermatitis, psoriasis, acne, ichthyosis, contact dermatitis, eczema, photodermatoses and dry skin disorders (particularly selected from one or more of atopic dermatitis, acne, ichthyosis, contact dermatitis, eczema, photodermatoses and dry skin disorders, more particularly selected from one or more of atopic dermatitis, acne, ichthyosis, contact dermatitis, photodermatoses and dry skin disorders, especially atopic dermatitis).

According to another aspect of the present invention, there is provided a nutritional product (or nutraceutical) for use in the prevention and/or treatment of atopic dermatitis in a subject, wherein the nutritional product comprises a therapeutically effective amount of histidine and/or a derivative thereof as the active ingredient. There is also provided the use of histidine and/or a derivative thereof in the manufacture of a nutritional product (or nutraceutical) for use in the prevention and/or treatment of atopic dermatitis in a subject.

According to the present invention, there is also provided a method for preventing and/or treating atopic dermatitis in a subject in need thereof, which method comprises administering to said subject a therapeutically effective amount of a nutritional product (or nutraceutical) comprising a therapeutically effective amount of histidine and/or a derivative thereof as the active ingredient.

The nutritional product may take any suitable form, such as a beverage or drink, a powder or powder mix, a food bar or other solid foodstuff, and may include any additional suitable ingredient(s) as well as the active ingredient. Such additional ingredients may be added for nutritional or medical reasons or for improved palatability. For example, a solid form of the histidine and/or the derivative thereof, such as in the form of a powder, may be incorporated into a solid foodstuff such as a food bar (for example a fruit bar, nut bar or cereal bar). For presentation in the form of a food bar, the powder can be admixed with any one or more ingredients selected from dried fruits such as sundried tomatoes, raisins and sultanas, ground nuts or cereals such as oats and wheat. For presentation in the form of a beverage or drink, the powder can be admixed with any one or more ingredients such as water, fruit juice and/or flavouring. A solid form of the histidine and/or the derivative thereof, such as in the form of a powder, may be provided, optionally admixed with any one or more further ingredients, (for example in a suitable packaging, such as a sachet) for addition to a liquid for consumption by a subject.

Therapeutically effective amounts of histidine and/or the derivative thereof in a nutritional product may be as described above in relation to pharmaceutical compositions, particularly in relation to the pharmaceutical compositions formulated for oral administration.

A suitable nutritional product may comprise:
(a) a clear, low viscosity, water-like, stable, ready-to-use, bottled, carbonated or non-carbonated drink; or a concentrated clear liquid for reconstitution containing histidine and/or a derivative thereof;
(b) a powder/granular mix to be reconstituted with water or any other orally ingestible liquid as a drinkable liquid, containing histidine and/or a derivative thereof;
(c) a powder/granular mix mixed into a foodstuff (for example a food bar or the like). Conventional procedures known the persons skilled in the art may be used to create the nutritional products or nutraceuticals, such as in the form of liquid drinks, powder mixes and foodstuffs, comprising the histidine and/or the derivative thereof.

The amount of the active ingredient required by a subject, for example as a daily dose, is determined by biological activity and bioavailability which in turn depends on the formulation, mode of administration, the physicochemical properties of the active ingredient and whether the active ingredient is being used as a monotherapy or in a combined therapy. Generally, a daily dose for a human adult should be between 0.1 g and 100 g of the active ingredient (however formulated), more preferably between 1 g and 30 g (for example about 5 g, 10 g, or 15 g as required).

The frequency of administration will also be influenced by the above-mentioned factors and particularly the half-life of the active ingredient within the subject being treated. For instance, the half-life will be influenced by the health status of the subject, gut motility and other factors.

Daily doses may be given as a single administration (for example as a daily tablet, a capsule or liquid suspension or as a nutritional product for oral consumption). Alternatively doses may be given twice or more times during a day.

The pharmaceutical composition or nutritional product of the invention may be applied as a sole therapy or may be applied in combination with a conventional therapy, such as treatment with steroids (for example steroids for topical administration) and/or suitable lipids, and/or with phototherapy as discussed above. For example, the pharmaceutical composition or nutritional product of the invention may be applied in combination with phototherapy, such as narrow-band UVB phototherapy widely used to treat moderate to severe adult atopic dermatitis and discussed above.

The "subject" to which the active ingredient and/or pharmaceutical composition and/or nutritional product (or nutraceutical) of the invention is to be administered is an animal, by which we include mammals and birds. In particular, the subject may be a warm-blooded animal, such as a domestic animal or man, particularly man.

Histidine is an amino acid having the chemical name 2-amino-3-(3H-imidazol-4-yl)propanoic acid. Histidine exists in two enantiomeric forms, L-histidine and D-histidine, as shown below:

L-Histidine            D-Histidine

References herein to the generic term "histidine" include any scalemic or racemic mixture of the enantiomers (wherein a scalemic mixture contains the enantiomers in any relative proportions and a racemic mixture contains the enantiomers in the ratio 50:50), as well as L-histidine and/or D-histidine. References herein to individual enantiomers are specific to that enantiomer only. When a scalemic mixture is provided, the mixture preferably comprises more L-histidine than D-histidine, more preferably the mixture comprises mostly L-histidine. For example, the scalemic mixture may comprise at least 60%, more preferably at least 75%, even more preferably at least 90% by weight of L-histidine. References herein to the generic term "histidine" also include all tautomeric forms. Preferably, the histidine is L-histidine and/or a derivative thereof. L-histidine occurs naturally and is readily obtainable from natural sources.

The histidine may be synthesised from suitable starting materials using standard procedures of organic chemistry or may be isolated from natural sources using well known procedures. The synthesis or isolation of particular enantiomers of histidine may be carried out by standard techniques of organic chemistry well known in the art, for example by synthesis from optically active starting materials or by resolution of a racemic form for example by suitable well known techniques.

L-histidine may for example be isolated from any suitable source, such as from meat, poultry, dairy, fish, rice, wheat and rye.

Histidine may be provided as a solid or semi-solid, preferably as a powder.

Any suitable derivative of histidine may be used in the present invention, provided that the derivative is suitable for including in a pharmaceutical composition and provides the desired pharmacological effect as discussed herein. Combinations of histidine and suitable derivatives thereof may be used. The derivatives of histidine may be synthesised from suitable starting materials using standard procedures of organic chemistry or may be isolated from natural sources using well-known procedures.

Suitable derivatives of histidine may be comprised predominantly of a histidine core with minor modifications to functional groups of the histidine core. For example, references herein to derivatives of histidine include compounds derived from histidine (i.e. having a histidine core) in which the carboxylic acid or amino group of the histidine core is derivatised to include a substituent or alternative functional group. For example, suitable derivatives in which the hydroxy group of the carboxylic acid group is derivatised may include an ester (such as an ester formed by the reaction of the carboxylic acid and an alcohol such as methanol, ethanol, isopropanol or butanol). Suitable derivatives in which the amino group is derivatised may include a dialkyl- or trialkyl-amine (such as a dialkyl- or trialkyl-amine formed by the reaction of the amino group and an alkyl-halide).

Further suitable derivatives of histidine include peptides of histidine, such as peptides including 2 or more histidine units, for example from 2 to 20 histidine units, particularly from 2 to 10 histidine units or from 7 to 10 histidine units, or for example 20 or more histidine units. Particular such derivatives may be di- and tri-peptides of histidine.

Further suitable derivatives of histidine include peptides of histidine and one or more additional amino acids, such as peptides including 2 or more histidine/additional amino acid units, for example from 2 to 20 histidine/additional amino acid units, particularly from 2 to 10 histidine/additional amino acid units or from 7 to 10 histidine/additional amino acid units, or for example 20 or more histidine/additional amino acid units. Particular such derivatives may be di- and tri-peptides, such as a dipeptide of histidine and beta-alanine (otherwise known as carnosine).

Further suitable derivatives may include, for example, pharmaceutically-acceptable salts or pro-drugs of histidine and the functionalised compounds or polypeptides as discussed above. By the term pro-drug we mean a compound that is broken down in a subject, for example in a warm-blooded animal such as man, to release the histidine and/or the derivative thereof. Examples of pro-drugs may include in vivo cleavable ester derivatives such as those described above. Suitable pharmaceutically-acceptable salts and pro-drugs are based on reasonable medical judgement as being suitable for administration to a subject, for example a warm-blooded animal such as man, without undesirable pharmacological activities and without undue toxicity. Examples of suitable pharmaceutically-acceptable salts include acid-addition salts with an inorganic or organic acid such as hydrochloric, hydrobromic, sulfuric, trifluoroacetic, citric or maleic acid.

In all aspects of the present invention as described herein any derivative of histidine is preferably selected from one or more of a peptide of histidine (particularly di- and tri-peptides of histidine), a peptide of histidine and one or more additional amino acids (particularly di- and tri-peptides, for example carnosine), and a pharmaceutically-acceptable salt of histidine. More preferably, any derivative of histidine is selected from one or more of a di- or tri-peptide of histidine, a di- or tri-peptide of histidine and one or more additional amino acids (for example carnosine), and a pharmaceutically-acceptable salt of histidine. Even more preferably, any derivative of histidine is a pharmaceutically-acceptable salt of histidine.

Most preferably, in all aspects of the present invention as described herein, the active ingredient is histidine, more preferably L-histidine. In other words, the present invention preferably provides histidine (more preferably L-histidine) for use in maintaining and/or improving barrier function of the skin of a subject and for the prevention of a skin disorder (particularly an inflammatory skin disease, more particularly a chronic inflammatory skin disease, and even more particularly atopic dermatitis) as described herein, as well as pharmaceutical compositions and nutritional products comprising histidine (more preferably L-histidine) as described herein.

The invention will now be illustrated by the following non-limiting Examples.

Example 1

A typical ointment for topical administration may contain:

| Ingredient | % w/w |
|---|---|
| L-Histidine | 1.0 |
| Emusifying Ointment BP (White Soft Paraffin, Liquid Paraffin, Emusifying Wax mixture) | 30.0 |
| Isopropyl Myristate | 5.0 |
| Hydroxyethylcellulose | 0.2 |
| Glycerol | 1.0 |
| Phenoxyethanol | 1.0 |
| Purified Water | 61.8 |

Example 2

A typical ointment for topical administration may contain:

| Ingredient | % w/w |
|---|---|
| L-Histidine | 2.0 |
| Emusifying Ointment BP (White Soft Paraffin, Liquid Paraffin, Emusifying Wax mixture) | 30.0 |
| Isopropyl Myristate | 5.0 |
| Hydroxyethylcellulose | 0.2 |
| Glycerol | 1.0 |
| Phenoxyethanol | 1.0 |
| Purified Water | 60.8 |

Example 3

A typical ointment for topical administration may contain:

| Ingredient | % w/w |
|---|---|
| L-Histidine | 1.0 |
| Hydroxyethylcellulose | 2.0 |
| Propylene Glycol | 20.0 |
| Phenoxyethanol | 1.0 |
| Purified Water | 76.0 |

Example 4

A typical ointment for topical administration may contain:

| L-histidine | 2.5 g |
|---|---|
| Polyethylene glycol 1500 | 5.0 g |
| Polyethylene glycol 4000 | 15.0 g |
| Polyethylene glycol | ad 100.0 g |

Example 5

A typical tablet, which may be prepared by conventional tableting techniques (for example by compression), may contain:

| Core: | |
|---|---|
| L-histidine | 200 to 500 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | about 9 mg |
| Mywacett 9-40 T** | about 0.9 mg |

*Polacrillin potassium NF, Tablet disintegrant, Rohm and Haas
**Acylated monoglyceride used as plasticizer for film coating Example 6

A nutritional product in the form of a free-flowing powder formulation (containing 5.0 g of L-histidine) that is suitable for packaging in a sachet was prepared. The powder mix may be diluted to taste and drunk when required by a subject suffering from a skin disorder.

The powder formulation was prepared by mixing 5.0 g of powdered L-histidine and 0.2 g of a standard spray-dried mix of flavouring.

Example 7

A nutritional product in the form of a free-flowing powder formulation (containing 3.0 g of L-histidine) that is suitable for packaging in a sachet was prepared. The powder mix may be diluted to taste and drunk when required by a subject suffering from a skin disorder.

The powder formulation was prepared by mixing 3.0 g of spray-dried L-histidine with 0.5 g powdered citric acid, 26.3 g of granulated sugar and 0.2 g of a standard spray-dried mix of flavouring.

Example 8

A nutritional product in the form of an orange drink (containing 3.0 g of L-histidine) was prepared as follows:
(a) 3.5 g of freeze-dried L-histidine (powder) was dissolved in 100 ml of orange juice (or alternatively with orange juice concentrate and water); or
(b) 2.5 g of freeze-dried L-histidine (powder) was dissolved in 100 ml of orange juice (or alternatively with orange juice concentrate and water).

The orange drink preparations (a or b) may be consumed by a subject immediately, refrigerated for later consumption or sealed in a bottle or carton for a longer shelf life. It will be appreciated that orange juice may be readily substituted with a palatable alternative.

Example 9

A randomised, double-blind, placebo-controlled study was conducted as follows:

Adult (i.e. greater than 18 years of age) patients with moderate to severe chronic atopic dermatitis were recruited to the study from patients and diagnosis of atopic dermatitis confirmed using the UK Working Party's Diagnostic criteria (see Williams et al, *Br. J. Dermatol.* 1994; 131:383-96). Exclusion criteria were: patients aged less than 18 years, pregnancy or lactation, liver disease, exposure to natural or artificial ultra-violet radiation, immunosuppression due to disease or medication and Chinese herbal medicine in the 3 months preceding the study. Patients were asked to cease potent topical steroid use during the study. Disease severity was quantified by a research nurse using the well established SCORAD system (see Schmitt et al, European Dermato-Epidemiology Network, *J. Allergy Clin. Immunol.*, 2007; 120:1389-98) and self assessed by the patients using POEM (Patient-Oriented Eczema Measure; see Charman et al, *J. Arch. Dermatol.* 2004; 140-1513-9). Skin barrier function was assessed using a Vapometer® which quantifies Trans Epidermal Water Loss (TEWL; see Fluhr et al, *Exp. Dermatol.*, 2006; 15:483-92).

Atopic dermatitis patients were randomised into each of 2 groups and after a 'washout' period of 2 weeks and received either 4.0 g of powder L-histidine or 4.0 g of placebo (the naturally occurring food sweetener, erythritol) powder daily for 4 weeks. The patients were instructed to dissolve either the L-histidine or placebo powder in fruit juice. Neither the patient nor the clinical staff was aware of the identity of treatments administered.

The results obtained are as follows:

|  | 4.0 g L-Histidine | 4.0 g Placebo |
|---|---|---|
| n | 4 | 3 |
| SCORAD before | 37 | 34 |
| SCORAD after 4 wks | 25 | 34 |
| SCORAD % change after 4 wks | −22 | 0 |
| TEWL before | 16 | 15 |
| TEWL after 4 wks | 8 | 15 |
| TEWL % change after 4 wks | −50 | 0 |
| POEM before | 20 | 20 |
| POEM after 4 wks | 15 | 19 |
| POEM % change after 4 wks | −25 | −5 |

The results show that 4 weeks of 4.0 g L-histidine daily reduced clinician-scored disease activity (SCORAD) by 22%, transepidermal water loss (TEWL) by 50% and patient-scored disease activity by 25%. In contrast, no reduction in clinician-scored disease activity (SCORAD) and transepidermal water loss (TEWL) and minimal reduction (5%) in patient-scored disease activity was seen in the placebo group.

Example 10

The following gel was prepared, including 2% w/w of L-histidine:

| Ingredient | % w/w |
|---|---|
| L-Histidine | 2.0 |
| Hyroxyethylcellulose | 1.8 |
| Propylene Glycol | 20.0 |
| Phenoxyethanol | 1.0 |
| Purified Water | 75.2 |

A male subject with scaly, erythematous, pruritic (itchy) dermatitis received a twice daily application of the gel (containing 2% w/w of L-histidine) for a period of 19 days. The results of the treatment are shown in the photographs provided as FIGS. 2A, 2B, 2C and 2D (for application of the gel on days 1, 6, 13 and 19).

Figure 2A:
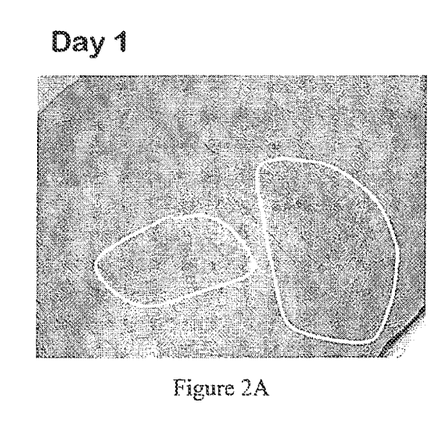
FIGS. 2A through 2D depict an area of skin treated with the gel of Example 10 at various times after application of the gel.
Figure 2B:
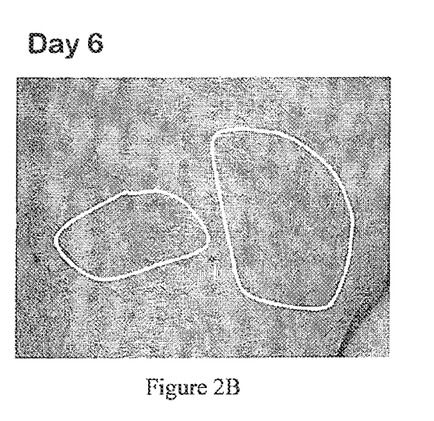
Figure 2C:
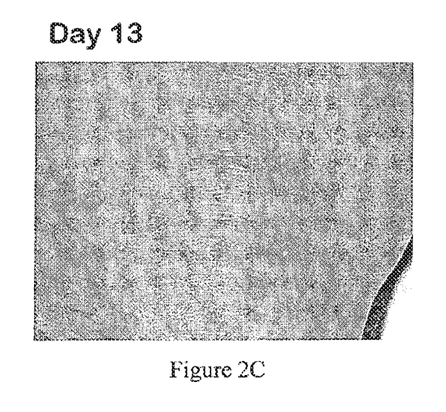
Figure 2D:
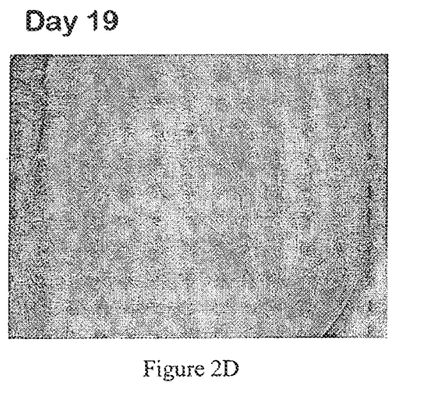

On commencing gel application there was marked dermatitis which was itchy, scaly and erythematous (circled in FIG. 2A). After 6 days application, the scaling and itchiness had subsided and only residual erythema remained (circled in FIG. 2B). By day 13 of daily application of 2% L-histidine gel very little evidence of scaling or erythema characteristic of dermatitis remained (see FIG. 2C) and itching had ceased. After 19 days of this treatment all skin signs and symptoms of dermatitis had completely resolved (see FIG. 2D).

Example 11

A randomised, double-blind, placebo-controlled study is conducted as follows:

Adult (i.e. greater than 18 years of age) patients with moderate to severe chronic atopic dermatitis are recruited to the study from patients and diagnosis of atopic dermatitis confirmed using the UK Working Party's Diagnostic criteria (see Williams et al, *Br. J. Dermatol.* 1994; 131:383-96). Exclusion criteria are: patients aged less than 18 years, pregnancy or lactation, liver disease, exposure to natural or artificial ultra-violet radiation, immunosuppression due to disease or medication and Chinese herbal medicine in the 3 months preceding the study. Disease severity is quantified by a research nurse using the well established SCORAD system (see Schmitt et al, European Dermato-Epidemiology Network, *J. Allergy Clin. Immunol.*, 2007; 120:1389-98) and self assessed by the patients using POEM (Patient-Oriented Eczema Measure; see Charman et al, *J. Arch. Dermatol.* 2004; 140-1513-9). Skin barrier function is assessed using a Vapometer® which quantifies Trans Epidermal Water Loss (TEWL; see Fluhr et al, *Exp. Dermatol.*, 2006; 15:483-92) and skin pH is measured using an appropriate meter (see Ehlers et al, *Skin Res. Technol.* 2001; 7:84-9). Patients are asked to cease potent topical steroid use during the study and, in groups 4 and 5 only to use non-UVB absorbing emollients such as emulsifying ointment or aqueous cream (see Reynolds et al, *Lancet* 2001: 357:2012-6).

Atopic dermatitis patients are randomised into each of 5 groups and after a 'washout' period of 2 weeks topical or oral treatment is commenced as shown below:

In order to determine whether oral histidine has a beneficial effect on atopic dermatitis patients, after the two week wash-out period, patients who are randomised into groups 2 and 3 are supplied with identical capsules containing either 500 mg pharmaceutical grade L-histidine or placebo. Subjects are advised to take either 4 g of L-histidine or placebo daily (in either capsule, tablet or powder form). After 8 weeks the oral treatment is crossed-over so that those patients taking placebo start taking active and vice versa. Every four weeks comparative measurements of SCORAD, skin UCA levels, pH and TEWL between groups 2 and 3 are conducted to determine the beneficial effects of oral L-histidine on disease severity and skin barrier function. Additionally, for each week of the study subjects are asked to complete a POEM form as a more general measure of disease severity.

| GROUP (n) | SCORAD POEM Forearm TEWL, pH, UCA | Weeks 1-2 (Washout) | SCORAD POEM Forearm TEWL, pH, UCA | Weeks 3-6 | SCORAD POEM Forearm TEWL, pH, UCA | Weeks 7-10 | SCORAD POEM Forearm TEWL, pH, UCA | Weeks 11-14 | SCORAD POEM Forearm TEWL, pH, UCA | Weeks 15-18 | SCORAD POEM Forearm TEWL, pH, UCA |
|---|---|---|---|---|---|---|---|---|---|---|---|
| 1 (12) | + + | POEM | + + | topical placebo to one forearm / topical active to other forearm | + + | — | — | — | — | — | — |
| 2 (8) | + + | POEM | + + | oral placebo POEM | + + | oral placebo POEM | + + | oral active POEM | + + | oral active POEM | + + |
| 3 (8) | + + | POEM | + + | oral active POEM | + + | oral active POEM | + + | oral placebo POEM | + + | oral placebo POEM | + + |
| 4 (10) | + + | POEM | + + | oral placebo POEM | + + | oral placebo UVB PRx POEM | + + | oral placebo UVB PRx POEM | + + | oral placebo UVB PRx POEM | + + |
| 5 (10) | + + | POEM | + + | oral active POEM | + + | oral active UVB PRx POEM | + + | oral active UVB PRx POEM | + + | oral active UVB PRx POEM | + + |

In order to determine whether skin levels of trans-urocanic acid (trans-UCA) in atopic dermatitis correlate with loss of function of filaggrin gene (FLG) mutations in atopic dermatitis patients, initial skin UCA levels of recruited atopic dermatitis patients are measured. UCA is extracted from mid-lower back skin using a standard non-invasive method (see Jansen et al, *Acta Derm. Venereol.* 1991; 71:143-154 and McLoone et al, *J. Invest. Dermatol.* 2005; 124: 1071-4) and UCA isomer levels were assessed by HPLC (see Gibbs et al, *J. Rapid Communication, Photochem. Photobiol.* 1993; 57: 584-590). Levels of UCA isomers are correlated with POEM measured disease severity.

In order to determine whether topical histidine has a beneficial effect on skin barrier function atopic dermatitis patients, after the two week wash-out period, patients in group 1 are supplied with topical formulations of placebo and pharmaceutical grade L-histidine in packaging marked either 'LEFT' or 'RIGHT'. All subjects are advised to apply the topical formulations instead of their normal emollients on either their left or right forearms (randomised) twice daily for 4 weeks. For each week of the study subjects are asked to complete a POEM form. Comparative measurements of skin UCA levels, pH and TEWL on placebos versus active forearms are used to determine the beneficial effects of topical histidine of skin barrier function.

In order to determine whether oral histidine increases the efficacy of phototherapy, after the two week wash-out period, patients in groups 4 and 5 are supplied with identical capsules containing either 500 mg pharmaceutical grade L-histidine or placebo. All subjects are advised to take 4 g of L-histidine or placebo daily. They then start a standard course of TL-01 phototherapy as conducted at the Manchester Dermatology Centre. Every four weeks comparative measurements of SCORAD, skin UCA levels, pH and TEWL between groups 4 and 5 are conducted to determine the beneficial effects of oral L-histidine on the response of atopic dermatitis to phototherapy and also record any combined effects of L-histidine and phototherapy on skin barrier function. Additionally, for each week of the study subjects are asked to complete a POEM form as a more general measure of disease severity.

What is claimed is:
1. A method of treating atopic dermatitis, the method comprising:
   administering orally to a human adult subject suffering from atopic dermatitis as a single daily dose a composition comprising 4 g of L-histidine and/or a pharmaceutically acceptable salt thereof in a liquid in the form of a suspension,
   the atopic dermatitis being treated.

2. A method according to claim 1, the oral composition comprising a glycol.

3. A method according to claim 1, the oral composition comprising glycerol.

4. A method according to claim 1 in which the oral composition comprises citric acid.

5. A method according to claim 1 comprising exposing skin of the subject to ultraviolet radiation.

6. The method according to claim 1, wherein the administering of the single daily dose is carried out for at least 4 weeks.

7. The method of claim 1, wherein L-histidine is the sole active ingredient.

8. A method of treating atopic dermatitis, the method comprising:
   administering orally to a human child subject suffering from atopic dermatitis as a single daily dose a composition comprising 0.2 to 1 g of L-histidine and/or a pharmaceutically acceptable salt thereof in a liquid in the form of a suspension,
   the atopic dermatitis being treated.

9. A method according to claim 8, the oral composition comprising pectin.

10. A method according to claim 8 in which the oral composition comprises citric acid.

11. A method according to claim 8 comprising exposing skin of the subject to ultraviolet radiation.

12. A method according to claim 8 comprising administering orally to a human child subject suffering from atopic dermatitis as a single daily dose a composition comprising 0.8 g of L-histidine and/or a pharmaceutically acceptable salt thereof.

13. The method according to claim 8, wherein the administering of the single daily dose is carried out for at least 4 weeks.

14. The method of claim 8, wherein L-histidine is the sole active ingredient.

15. A method of treating atopic dermatitis, the method comprising:
   administering orally to a human adult subject suffering from atopic dermatitis as a single daily dose a composition comprising 4 g of L-histidine and/or a pharmaceutically acceptable salt thereof in (i) a solid carrier comprising a gel or (ii) a dispersed powder,
   the atopic dermatitis being treated.

16. The method of claim 15, in which the oral composition comprises citric acid, sweetener and a flavouring agent.

17. A method of treating atopic dermatitis, the method comprising:
   administering orally to a human child subject suffering from atopic dermatitis as a single daily dose a composition comprising 0.2-1 g of L-histidine and/or a pharmaceutically acceptable salt thereof in (i) a solid carrier comprising a gel or (ii) a dispersed powder,
   the atopic dermatitis being treated.

18. The method according to claim 17, wherein the oral composition comprises 0.8 g, of L-histidine and/or a pharmaceutically acceptable salt thereof.

19. The method of claim 17, in which the oral composition comprises citric acid, sweetener and a flavouring agent.

20. The method of claim 17, in which the gel comprises pectin.

* * * * *